United States Patent [19]

Ichikawa et al.

[11] 4,230,584
[45] Oct. 28, 1980

[54] LIQUID SEPARATING COMPOSITION AND APPARATUS FOR APPLYING SAID COMPOSITION

[75] Inventors: Toshizi Ichikawa; Teruko Watanabe, both of Tokyo, Japan

[73] Assignee: Terumo Corporation, Himonya, Japan

[21] Appl. No.: 10,484

[22] Filed: Feb. 8, 1979

Related U.S. Application Data

[62] Division of Ser. No. 843,950, Oct. 20, 1977, Pat. No. 4,172,803.

[30] Foreign Application Priority Data

Oct. 21, 1976 [JP] Japan ............................. 51-126688
Oct. 21, 1976 [JP] Japan ............................. 51-126689
Jan. 8, 1977 [JP] Japan ............................. 52-1094

[51] Int. Cl.³ ........................................... B01D 21/26
[52] U.S. Cl. ................................... 210/516; 210/927; 233/1 A; 233/26
[58] Field of Search ............. 233/1 R, 1 A, 26, ; 252/60, 316; 128/272, 272.3, 763, 764; 210/83, 84, 514–518, DIG. 23, DIG. 24

[56] References Cited

U.S. PATENT DOCUMENTS

| 2,676,925 | 4/1954 | Lindstrom | 252/309 |
|---|---|---|---|
| 3,654,925 | 4/1972 | Holdeeith | 210/DIG. 23 |
| 3,941,171 | 3/1976 | Ogle | 128/272.3 |
| 3,963,119 | 6/1976 | Lukas | 252/60 |
| 3,977,982 | 8/1976 | Hertl | 252/316 |
| 3,986,962 | 10/1976 | Kessler | 210/DIG. 23 |
| 4,021,340 | 5/1977 | Zine | 210/DIG. 23 |
| 4,049,692 | 9/1977 | Zine | 252/316 |
| 4,140,631 | 2/1979 | Okuda | 210/DIG. 23 |
| 4,152,269 | 5/1979 | Babson | 210/DIG. 23 |

FOREIGN PATENT DOCUMENTS 1456517 11/1973 United Kingdom ................. 128/272.3

Primary Examiner—Ernest G. Therkorn
Attorney, Agent, or Firm—Bacon & Thomas

[57] ABSTRACT

This invention provides a liquid separating composition containing as a base material a liquid polymer of hydrocarbon or derivatives thereof having a viscosity ranging from 100 to 20,000 CP at 20° C., suitable amounts of additives for adjusting the specific gravity and viscosity of the composition and a netword former for imparting a thixotropic property to the composition. This invention also provides an apparatus for applying a liquid separating composition, comprising a vessel filled with a liquid separating composition, and a cannula fixed to the vessel, for piercing into a rubber cap of a liquid container.

The liquid separating composition is transferred to the liquid container by centrifuging the apparatus connected to the liquid container.

4 Claims, 11 Drawing Figures

LIQUID SEPARATING COMPOSITION AND APPARATUS FOR APPLYING SAID COMPOSITION

This is a continuation, division of application Ser. No. 843,950, filed 10/20/77 now U.S. Pat. No. 4,172,803.

BACKGROUND OF THE INVENTION

This invention relates to a liquid separating composition used for centrifugal separation of a liquid substance consisting of at least two components having different specific gravities and to an apparatus for applying the composition to the liquid substance to be separated.

It is widely known to the art to separate centrifugally a liquid substance consisting of at least two components having different specific gravities into component layers. For example, the whole blood collected in a test tube for the blood examination is subjected to centrifugal separation so as to isolate the blood serum and the blood plasma from the blood corpuscle for an analytical purpose. For this whole blood separation, it is known to use a liquid separating composition (or a barrier) having a specific gravity intermediate between those of the blood serum and the blood corpuscle. The liquid separating composition mentioned is filled in advance in an evacuated test tube in which the whole blood is to be collected to added to the whole blood collected in a test tube.

For example, U.S. Pat. No. 3,852,194 discloses an evacuated blood collecting tube having a gel-like liquid separating composition positioned in advance at the bottom portion. U.S. Pat. No. 3,780,935 discloses another type of device. In this case, a vessel containing a liquid separating composition and provided with a nozzle at the bottom is mounted on the opening of a test tube filled in advance with the whole blood. The assembly of the vessel and the test tube is rotated so as to enable the liquid separating composition to be injected centrifugally through the nozzle of the vessel into the whole blood collected in the test tube.

In the prior art mentioned first, the composition positioned in the bottom of the test tube is caused to rise up to the central portion of the test tube in the subsequent step of centrifugal separation of the whole blood. A major problem inherent in this technique is that collision takes place between the rising composition and the solid components of the blood, resulting in destruction of blood corpuscles to cause hemolysis. Another difficulty to be noted is that fibrin is partially included in the separated serum portion because a barrier layer consisting of the liquid separating composition is merely advanced up to the intermediate portion of the blood layers.

In the other prior art, i.e., U.S. Pat. No. 3,780,935, a rubber stopper of the tube containing the whole blood is removed first and, then, the vessel having the composition is mounted on the opening of the blood tube in preparation for the subsequent operation of centrifugal separation. In this case, the blood collected in the tube is brought into direct contact with the atmosphere because the stopper of the tube is removed first an the opening of the blood tube is not sealed air-tight by the vessel mounted thereon. It follows that the blood may possibly be contaminated by bacteria present in the atmosphere. In addition, this prior art involves troublesome blood separating operations including the removal of the rubber stopper and the mounting of the vessel containing the liquid separating composition on the opening of the blood tube. It should also be noted that the operator may possibly be infected by pathogenic organs contained in the blood because the rubber stopper touched by the operator is dotted with stains of the blood in many cases.

U.S. Pat. No. 3,780,935 mentioned above also teaches a liquid separating composition used for separation of a liquid substance, said composition being provided by a gel-like mixture of a silicone fluid and a hydrophobic silicon dioxide. The composition exhibits fluidity when subjected to centrifugal operation, moves into the boundary between the phases which are to be separated, and forms a stable barrier layer sandwiched between the phases after completion of the centrifugal operation. However, this liquid separating composition is not satisfactory in that the silicone fluids reacts on the surface of the silica grain as described in detail in U.S. Pat. No. 3,977,982, resulting in decrease with time of viscosity of the composition. Accordingly, when the test tube housing the phase-separated blood is inclined for taking out the separated blood serum portion, the barrier layer formed of the liquid separating composition is mixed into the serum portion. Naturally, it gives a bad influence to the accuracy in the analysis of the separated blood serum. Further, it is undesired to preserve the test tube containing the blood whose phases have been separated by the barrier layer of a decrease viscosity.

Another difficulty to be noted is that the liquid separating composition contains a silicone fluid as a major component as mentioned previously, which brings about a lowered blood coagulation speed. Thus, a secondary treatment for promoting the blood coagulation is required in order to shorten the blood examination time. Further, such a large stress as at least about 1,100 G is required in the centrifugal separation step, presenting a cause of hemolysis. Still further, it is necessary to use an expensive centrifuge capable of high speed rotation. It is also noted that, when silicone fluid is irradiated with γ-rays for the purpose of sterilization, the silicone fluid becomes too hard to centrifugal separation.

SUMMARY OF THE INVENTION

This invention has been achieved to overcome the difficulties inherent in the prior arts in this field. Specifically, an object of this invention is to provide a liquid separating composition having a thixotropic property, (i.e., easily exhibiting fluidity during a centrifugal operation, easily movable into the boundary between the phases which are to be separated, and forming a stable gel after completion of the centrifugal operation), small in change with time of viscosity during a long period of preservation in either the air or vacuum, and suitable for promoting the blood coagulation.

Another object is to provide an apparatus for supplying the liquid separating composition, free from the problems of hemolysis and fibrin mixing into the blood serum layer when used for the whole blood separating operation, quite easy in handling, and capable of keeping clean the blood in the separating operation.

According to this invention, there is provided a liquid separating composition containing as a base material a liquid polymer of hydrocarbon having a viscosity ranging from 100 CP to 20,000 CP at 20° C., suitable amounts of additives for adjusting the specific gravity and viscosity of the composition and a network former for imparting a thixotropic property to the composition.

This invention also provides an apparatus for applying a liquid separating composition, comprising a vessel having one end closed and filled with a liquid separating composition whose specific gravity has been adjusted to be intermediate between those of the phases of a liquid substance to be separated, and a cannula extending outward from the other end of the vessel, communicating with the interior of the vessel, and having a sharpened tip portion. The sharp edge of the cannula is inserted through an elastic stopper of a liquid container filled with a multiphase liquid collected in advance, so as to mount the apparatus to the liquid container. When a predetermined magnitude of centrifugal force is applied to the assembly of the apparatus for supplying a liquid separating composition and the multiphase liquid container the composition is transferred into the liquid container, thereby forming a barrier layer separating at least two phases of the liquid substance having differing specific gravities.

DETAILED DESCRIPTION OF THE PREFERRED EMBODIMENTS

Figure 1:
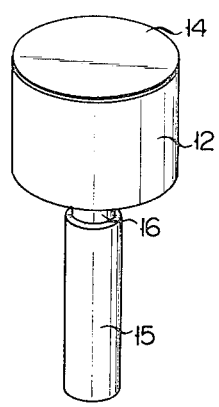
FIG. 1 is a perspective view of an apparatus for supplying a liquid separating composition to a tube containing a liquid substance to be separated according to one embodiment of this invention.

As mentioned above, FIGS. 1 and 2 collectively show an apparatus for supplying a liquid separating composition into a multiphase liquid tube, according to one embodiment of this invention. It is seen that the apparatus comprises a cup-shaped vessel 12 filled with a liquid separating composition 11, a cylindrical cannula 13 extending downward from the central portion of the bottom of the vessel body 12, and a lid 14 closing the upper opening of the vessel body 12. Further, a cap 15 for protecting the cannula 13 is detachably mounted to a hub 16 provided at the bottom of the vessel body 12.

The vessel body 12 and the lid 14 are both made of a thermoplastic resin such as polypropylene, and the lid 14 bonded to the vessel body 12 by, principally, thermal fusion. The base portion of the cannula 13 communicates with the interior of the vessel body 12 and the tip portion thereof is cut aslant so as to provide a sharp edge facilitating the penetration of the cannula through a rubber stopper of a multiphase liquid tube as described later.

Figure 2:
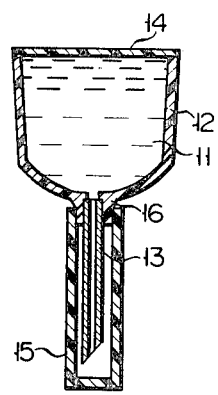
FIG. 2 is a cross sectional view of the apparatus shown in FIG. 1.
Figure 3:
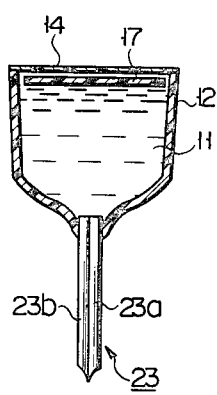
FIGS. 3 and 4 are cross sectional views of apparatuses for supplying a liquid separating composition, according to additional embodiments of this invention.

FIG. 3 shows an apparatus according to another embodiment of this invention. The apparatus of FIG. 3 differs from that of FIG. 2 in that a pressure plate 17 is disposed on the surface of the liquid separating composition 11 filled in the vessel body 12 and a cannula 23 is formed of two cylindrical cannulas 23a and 23b fastened together back to back. The pressure plate 17 serves to facilitate the injection of the liquid separating composition 11 through the tip of the cannula 23 during the centrifugal operation, because the centrifugal force exerted on the pressure plate 17 pushes the composition 11. Quite naturally, the pressure plate 17 is effective particularly where the liquid separating composition has a high viscosity. On the other hand, the cannula 23 consisting of a pair of cylindrical cannulas 23a and 23b is effective for releasing the air remaining inside a multiphase liquid tube during the centrifugal operation. Specifically, a small clearance between the cannulas 23a and 23b forms an air passageway when the cannula 23 is inserted into the multiphase liquid tube through a rubber stopper thereof. Thus, when the liquid separating composition 11 is centrifugally injected into the tube, the air remaining inside the tube is released through the air passageway.

Figure 4:
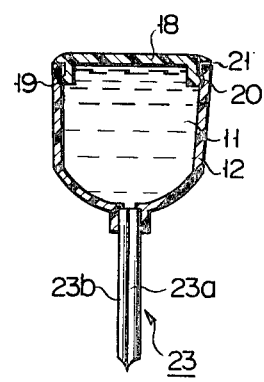

FIG. 4 shows an apparatus for supplying a liquid separating composition, according to another embodiment of this invention. The apparatus of FIG. 4 differs from that of FIG. 2 in the sealing fashion of the upper opening of the vessel body 12. Further, the cannula 23 is formed of a pair of cannulas 23a and 23b fastened together as in the cannula shown in FIG. 3.

In the apparatus of FIG. 3, an annular projection 19 formed along the circumferential side face of a lid 18 is engaged with an annular groove 20 formed in the upper portion of the inner wall of the vessel body 12 so as to close the upper opening of the vessel body 12. Further, a plurality of air passageways 21 capable of introducing the open air into the vessel body 12 are provided in the under face of the lid 18 at the peripheral portion. Incidentally, the cannula 23 of FIG. 4 is just the same in construction as the cannula 23 shown in FIG. 3. The apparatus of FIG. 4 is advantageous in that the air passageways 21 formed in the lid 18 facilitate injecting the liquid separating composition 11 through the cannula 23 during the centrifugal operation.

Figure 5:
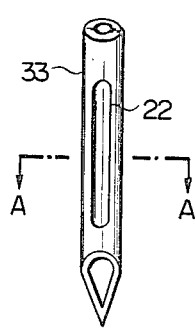
FIG. 5 is a perspective view of a cannula, according to another embodiment of this invention.
Figure 6:
FIG. 6 is the cross sectional view along the line A—A of FIG. 5.
Figure 7:
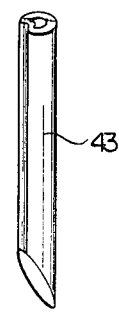
FIG. 7 is a perspective view of a cannula, according to another embodiment of this invention.
Figure 8:
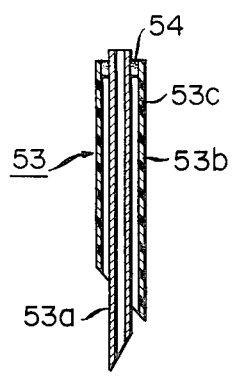
FIG. 8 is a cross sectional view of a cannula, according to still another embodiment of this invention.

FIGS. 5, 6 and 7 show modifications of the cannula fixed to the vessel body. It is seen that an axial groove 32 is formed on the outer wall of cannula 33 or 43, partially or over the entire length of the cannula. The axial groove 22 serves to form an air passageway when the cannula has been penetrated through a rubber stopper of a multiphase liquid tube, thereby permitting the air remaining inside the tube to be released through the air passageway during the centrifugal operation. FIG. 8 shows another modification of the cannula. In this case, a cannula 53 is of a double wall structure consisting of an inner tube 53a and an outer tube 53b. As shown in the drawing, the base portions of these tubes are bonded together with an adhesive 54 and an air inlet port 53c is formed in the upper portion of the outer tube 53b.

Each of the cannulas shown in FIGS. 3 to 8 is intended to form an air passageway when inserted through a rubber stopper of a multiphase liquid tube so as to facilitate releasing the air remaining inside the tube and to facilitate injecting the liquid separating composition into the tube. However, an ordinary cylindrical cannula as shown in FIG. 2 and having an inner diameter of 1.35 mm or more performs a satisfactory function, if the liquid separating composition housed in the vessel body has the properties as specified later.

The liquid separating composition according to this invention contains as a base material a liquid polymer of hydrocarbon or a liquid polymer of a derivative of hydrocarbon. It is preferred that the liquid polymer have a viscosity ranging between 100 CP at 20° C. and 20,000 CP at 20° C. as measured by a Brookfield Viscometer. It is also preferred in terms of preservation for a long time to apply maleinizing or epoxidizing treatment to the liquid polymer so as to prevent gellation, oxidation, etc. of the liquid polymer.

For example, the epoxidation treatment brings about agents including alkoxy silanes such as glycidoxy propyl trimethoxy silane.

Other examples of suitable network former are glycolsiloxane copolymer and di-benzal sorbitol dispersed in aromatic diester or aliphatic diester.

The liquid separating composition of this invention should be adjusted to have a specific gravity ranging between 1.030 and 1.065 and a viscosity ranging between 300,000 CP at 20° C. and 2,500,000 CP at 20° C., when used for isolating the blood serum or blood plasma from the whole blood. Table 1 below shows typical examples of the compositions meeting the above requirements:

TABLE 1

| Base material (100 parts by weight) | Additives (parts by weight relative to base material) | | | | | | |
|---|---|---|---|---|---|---|---|
| | Silica | Alumina | Diethylene- glycol | Glycol- siloxane copolymer | Di-benzal sorbitol*** | Nylon** | Barium sulfate* |
| Epoxidized liquid cis-polybutadiene | 3 | 0 | 2–5 | 0 | 0 | 0 | 0 |
| | 1.6 | 3.2 | 0 | 0 | 0 | 0 | 0 |
| | 2.5 | 2.5 | 0 | 0 | 0 | 0 | 0 |
| | 5.8 | 0 | 0 | 0 | 0 | 2.0 | 0 |
| | 4.0 | 0 | 0 | 1.8–3.0 | 0 | 0 | 0 |
| | 4.0 | 0 | 0 | 0 | 15–20 | 0 | 0 |
| Liquid polypropylene | 2.4 | 2.4 | 0 | 0 | 0 | 0 | 28 |
| Liquid polybutene | 2.4 | 2.4 | 0 | 0 | 0 | 0 | 27 |
| Liquid polyol | 5.0 | 8.2 | 0 | 0 | 0 | 0 | 0 |

Note:
*Fine powder of alumina and barium sulfate serve to increase the fluidity of the composition in the centrifugal separation step, facilitating the injection of the composition through the cannula of the apparatus for supplying the composition.
**A powdered nylon renders the composition opaque and, thus, the barrier layer formed of the composition is made clearly visible.
***Di-benzal sorbitol dispersed in aromatic diester or aliphatic diester.

an increased viscosity of the liquid polymer. In this case, the viscosity of the liquid polymer can be adjusted as desired by adding a small amount of a viscosity modifier. The epoxidation treatment also brings about an increased polarity of the liquid polymer, resulting in an increased compatibility of the liquid polymer. It follows that the liquid polymer subjected to epoxidation treatment is enabled to form a strong and stable barrier layer.

Suitable agents for adjusting the specific gravity and viscosity of the liquid polymer include, for example, inorganic powders such as hydrophilic or hydrophobic amorphous silica, alumina, barium sulfate and carbon black as well as powdered thermoplastic material like powdered nylon. These agents may be used singly or in combination and should be highly dispersive in the liquid polymer. In actually selecting the agent to be used, it is of course important to note that the agent should not give a detrimental effect to the liquid substance which is to be subjected to centrifugal separation.

The barrier layer separating the differing phases of a liquid substance should not be destructed by the vibrations in the transport of the liquid container or by the falling down of the container. To this end, a network former is added to the liquid polymer so as to impart thixotropic property to the liquid polymer. To be more specific, a gel-like liquid separating composition is imparted with thixotropic property if a suitable amount of a network former such as glycols is added to the composition. Namely, the composition is turned to sol if stress is applied thereto and returns to gel if stress is removed therefrom. As the result, the barrier layer formed of a thixotropic composition is tough enough to resist the vibrations mentioned above.

Suitable network formers serving to impart thixotropic property to the liquid separating composition comprise, for example, 1,3-propanediol, 1,4-butanediol, 1,5-pentanediol, diethylene glycol and silane coupling This invention is further explained as it is applied for separating the whole blood into the blood serum and the blood corpuscle.

Figure 9:
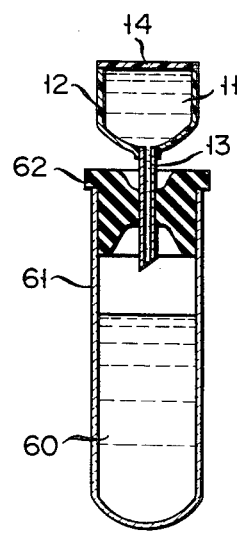
FIGS. 9 to 11 are cross sectional views of the assembly consisting of an apparatus for supplying a liquid separating composition and a tube housing a liquid to be separated, showing a process by which the liquid separating composition in said apparatus is transferred into said tube to form a barrier layer when the assembly is subjected to centrifugal operation.

As shown in FIG. 9, the cannula 13 of the apparatus for supplying a liquid separating composition pierces through a rubber stopper 62 of an evacuated tube 61 containing the whole blood 60 collected in advance. It is seen that the tip of the cannula 13 is positioned in the free space formed in the upper portion of the blood tube 61. As in an ordinary operation for isolating the blood serum or the blood plasma, the assembly consisting of the apparatus for supplying a liquid separating composition and the blood tube 61 connected in this fashion is subjected to centrifugal operation.

Figure 10:
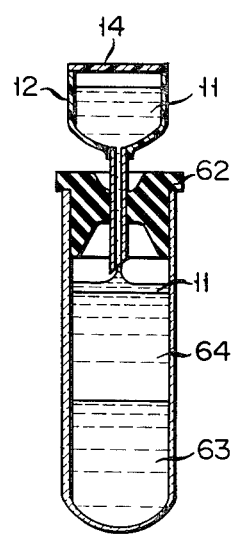

The gel-like liquid separating composition 11 is converted by application of the centrifugal force into a state of sol and, thus, exhibits fluidity and gradually flows into the blood tube 61 through the tip of the cannula 13. It is important to note that the composition 11 is controlled to enter the blood tube 61 after the blood corpuscle has sufficiently deposited in the lower portion as shown in FIG. 10. To this end, the components of the composition 11 are adjusted to enable the composition 11 to have a suitable specific gravity and a suitable viscosity, and the cannula 13 is designed to have 1.35 mm or more of inner diameter.

Figure 11:
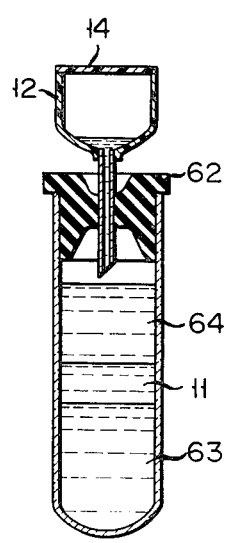

After completion of the centrifugal operation, almost all the liquid separating composition 11 filled in the vessel 12 is transferred into the blood tube 61 and forms a barrier layer 65 at the boundary between a blood corpuscle layer 63 and a blood serum layer 64 as shown in FIG. 11. Incidentally, the composition 11 which is in a state of sol, i.e., in a state of fluid, when subjected to the centrifugal force returns to a state of gel again after removal of the stress. The barrier layer 65 formed of the thixotropic composition 11 tightly adheres to the inner wall of the blood tube 61. Further, the barrier layer 65 is so strong as not to be destructed when the blood tube 61 has been turned upside down or vibrated. This permits safe transport of the blood tube 61 after the centrifugal operation to a clinical examination center. Further, the blood serum free from the mixing of the blood corpuscle layer 63 can be collected at a high quality by decantation of the blood tube 61.

As described previously, the base material of the liquid separating composition of this invention is provided by a liquid polymer of hydrocarbon type or a liquid polymer of a derivative from hydrocarbon, said liquid polymer having a viscosity ranging between 100 CP at 20° C. and 20,000 CP at 20° C. Typical examples of the liquid polymer used in this invention include liquid polybutadiene, liquid polypropylene and liquid polymer of a derivative from hydrocarbon. Clearly, the liquid separating composition of this invention can be prepared at a low cost, compared with the conventional liquid separating composition containing silicone oil, etc.

It should also be noted that the liquid separating composition of this invention is enabled to exhibit a relatively large thixotropy coefficient. Specifically, the composition is readily supplied to the blood tube if the centrifugal operation is carried out such that the centrifugal force applied to the blood is about 700 G. Accordingly, destruction of the blood corpuscle by an excessive stress can be substantially avoided in the step of centrifugal operation.

The invented apparatus for supplying the liquid separating composition is featured in that the composition can be supplied to a blood tube or the like without removing the elastic stopper of the tube. The feature mentioned is advantageous particularly where a poisonous or dangerous liquid substance is subjected to centrifugal separation. In the case of separating, for example, blood containing pathogenic organs, it is impossible that the pathogenic organs be scattered from the blood tube and attached to the operator. Likewise, bacteria present in the air do not enter the blood serum, permitting an accurate analysis of the blood serum.

Where a blood tube having the rubber stopper removed therefrom is subjected to centrifugal operation, it is of particularly high importance to note that the blood and the pathogenic organs contained therein are scattered in the form of mist into the open air because the interior pressure of the centrifuge is reduced by the centrifugal force. Naturally, this presents a serious problem with respect to the health of the operator. However, the apparatus for supplying the liquid separating composition according to this invention is free from the scattering problem of the pathogenic organs because the apparatus permits supplying the composition without removing the rubber stopper of the blood tube as described previously.

An additional merit produced by this invention is that, in the case of separating the whole blood, the liquid separating composition flows into the blood tube after the whole blood has been separated into the blood serum layer and the blood corpuscle layer. Specifically, the liquid separating composition descends through the separated blood serum layer down to the boundary between the blood serum layer and the blood corpuscle layer so as to form a barrier layer. Accordingly, the fibrin floating in the blood serum layer also descends together with the liquid separating composition, resulting in a high purity of the separated blood serum. It should also be noted that the liquid separating composition exerts pressure on the blood corpuscle layer in the course of forming a barrier layer. Thus, the blood serum remaining in the blood corpuscle layer is expelled into the blood serum layer, resulting in a high yield of the blood serum.

What is also important in this invention is that the apparatus for applying the liquid separating composition is very simple in structure. Particularly when using the liquid separating composition as mentioned in the Examples which follow, the cannula fixed to the vessel containing the liquid separating composition may be formed of a single hollow tube having an inner diameter of 1.35 mm or more, with quite satisfactory results. Naturally, it is unnecessary in this invention to use an air withdrawing mechanism of a complicated structure, which is used in the conventional apparatus for supplying a liquid separating composition. The simple structure achieved by this invention leads to a low manufacturing cost of the apparatus, which is prominently significant in this field of technique because the apparatus is generally thrown away after use only once.

EXAMPLE 1

A thixotropic composition having a specific gravity of about 1,048 and a viscosity of about 1,500,000 CP at 20° C. was prepared by blending 100 parts by weight of epoxidized poly-cis-butadiene having a specific gravity of 1,019 and a viscosity of 4,500 CP at 20° C., 5.5 parts by weight of Aerosil (trade name of hydrophobic silica powder having a specific gravity of 2.2, produced by Japan Aerosil Co., Ltd.) and 0.2 to 6 parts by weight of trimethylene glycol. Incidentally, the epoxidized poly-cis-butaeine mentioned was used as a liquid polybutadiene. The composition was stored in the air and under vacuum and changes with time in viscosity were measured, the results being shown in Table 2 below.

TABLE 2

| | Viscosity (CP × 10³) | |
| Time (weeks) | Air | Vacuum |
| --- | --- | --- |
| 0 | 1,400 | 1,400 |
| 1 | 1,450 | 1,450 |
| 5 | 1,500 | 1,400 |
| 10 | 1,500 | 1,450 |
| 15 | 1,600 | 1,450 |
| 25 | 1,650 | 1,450 |
| 30 | 1,650 | 1,450 |

The thixotropic composition in an amount of 2 cc was introduced in a test tube 12 mm in inner diameter and 10 cc in inner volume. The air in the test tube was then withdrawn, followed by collecting the whole blood in the test tube. The test tube containing both the thixotropic composition and the whole blood was rotated at 25,000 r.p.m. for 10 minutes at about 10 cm of radius of the circular motion for centrifugal separation of the blood, resulting in that a disk-like barrier layer about 2 cm thick was formed at the boundary between the blood serum layer and the blood corpuscle layer. The barrier layer was so stable that no damage to it was recognized scores of days later. Further, the barrier layer was not destructed at all when mechanical shocks such as vibration were given to the test tube.

An additional test was conducted in accordance with the procedures described above, except that maleinized poly-cisbutadiene having a specific gravity 24 of 1,016 and a viscosity of 4,500 CP at 20° C. was substituted for the epoxidized poly-cis-butadiene, obtaining the result substantially the same as in the case wherein epoxidized poly-cisbutadiene was employed as described above.

EXAMPLE 2

A liquid separating composition having a specific gravity of about 1,040 and a viscosity of about 1,500,000 CP at 20° C. was prepared by blending 100 parts by weight of liquid poly-cis-butadiene, 3 parts by weight of Aerosil mentioned in Example 1, and 5 parts by weight of diethylene glycol. The liquid poly-cis-butadiene used had been previously epoxidized by 50% with hydrogen peroxide, peracetic acid, etc. and had a specific gravity of 1,019 and a viscosity of 4,500 CP at 20° C.

The liquid separating composition was housed in a vessel made of polypropylene and constructed as shown in FIGS. 1 and 2. The bessel was provided with a cannula made of a steel tube 1.40 mm in inner diameter and about 0.1 mm in wall thickness.

On the other hand, 10 ml of the whole human blood was collected in an evacuated test tube 13.6 mm in inner diameter, 10 cm in length, 12.75 ml in inner volume and sealed with a rubber stopper.

The vessel housing the liquid separating composition was mounted to the blood tube as shown in FIG. 9 and the assembly was subjected to centrifugal operation under the same conditions as in Example 1. A blood serum layer and a blood corpuscle layer were formed first and, then, the liquid separating composition was seen to flow out of the tip of the cannula. The composition was gradually moved toward the blood corpuscle layer, finally forming a stable barrier layer about 1.5 cm thick at the boundary between the blood serum layer and the blood corpuscle layer.

EXAMPLE 3

Blood tubes containing serum separators consisting following compositions listed below were irradiated with γ-ray of 2.5 Mrad, and then introduced with plasma gel 3 cc and condensed red cell 4 cc and subsequently centrifused for ten minutes at 2,500 r.p.m. As a result, blood tube containing composition "A" or "B" showed clear separation of blood layers in the same manner as in the case where no irradiation is applied to the serum separator.

TABLE 3

| Composition | A | B |
| --- | --- | --- |
| Epoxidized liquid cis-polybutadiene | 100 | 100 |
| Anti-oxidant | 0.5 | 0.5 |
| Silica | 4 | 4 |
| Di-benzal sorbitol* | 15 | 0 |
| Glycol-siloxane copolymer | 0 | 1.8 |

Note:
*Di-benzal sorbitol dispersed in aromatic ester or aliphatic ester.

What is claimed is:

1. An apparatus for applying a liquid-separating composition to a multiphase liquid substance which is to be separated into two phases by means of a centrifugal force of a predetermined magnitude and is contained in a container closed by an elastic stopper which apparatus comprises a vessel having one end closed and being filled with a thixotropic liquid-separating composition having a specific gravity of from about 1.030 to about 1.065 which has been adjusted to be intermediate between those of the phases of the multiphase liquid to be separated, having a viscosity of from about 30,000 to about 2,500,000 CP at 20° C., and comprising a liquid polymer base material having a viscosity of from about 100 to about 20,000 CP at 20° C. selected from the group of liquid polybutadiene, liquid epoxidized polybutadiene and liquid maleinized polybutadiene, and a suitable amount of an additive for adjusting the specific gravity and the viscosity of the composition to the above ranges, and a thixotropic property-imparting amount of a network former;

and a cannula extending outward from the other end of the vessel, communicating with the interior of the vessel and having a sharpened tip portion which is to be inserted through the elastic stopper of the container as to mount the apparatus onto the container and provide a communication between the interior of the container and the vessel through which the liquid-separating composition is gradually transferable into the container upon application of the centrifugal force whereby the viscosity of the liquid-separating composition and the diameter of the cannula are adjusted such that the liquid-separating composition enters the container after sufficient separation of the phases of the multiphase liquid substance in the container has taken place.

2. The apparatus for applying a liquid-separating composition as defined in claim 1 wherein the additive for adjusting the specific gravity and viscosity is amorphous silica.

3. The apparatus for applying a liquid-separating composition according to claim 1, wherein the network former is selected from the group consisting of glycol, glycol-siloxane copolymer and di-benzal sorbitol dispersed in an ester selected from aromatic diester and aliphatic diester.

4. The apparatus for applying a liquid-separating composition according to claim 1, wherein the inner diameter of the cannula is 1.35 mm or more and the extended end of the cannula is sharpened.

* * * * *